US000001950H

(19) United States

(12) Statutory Invention Registration (10) Reg. No.: US H1950 H

Dumas (43) Published: Mar. 6, 2001

(54) PROCESSES FOR PREPARING INDENO[1,2-E][1,3,4]OXADIAZINE-DICARBOXYLATES

(75) Inventor: Donald J. Dumas, Wilmington, DE (US)

(73) Assignee: E. I. du Pont de Nemours and Company, Wilmington, DE (US)

(21) Appl. No.: 09/230,987

(22) PCT Filed: Jan. 31, 1997

(86) PCT No.: PCT/US97/13548

§ 371 Date: Feb. 3, 1999

§ 102(e) Date: Feb. 3, 1999

(87) PCT Pub. No.: WO98/05656

PCT Pub. Date: Feb. 12, 1998

Related U.S. Application Data

(60) Provisional application No. 60/022,426, filed on Aug. 5, 1996.

(51) Int. Cl.[7] ..... C07D 498/00

(52) U.S. Cl. ..... 540/548; 560/10; 560/16; 560/157

(58) Field of Search ..... 540/548

(56) References Cited

U.S. PATENT DOCUMENTS 5,500,438 * 3/1996 Barnette ..... 548/359

FOREIGN PATENT DOCUMENTS

WO92/11249 7/1992 (WO) .
WO93/19045 9/1993 (WO) .
WO95/29171 11/1995 (WO) .
95 29171 * 11/1995 (WO) .

OTHER PUBLICATIONS

A. Fruchier et al., Ourverture d'epoxydes par le N–hydroxy-carbamates de methyle; syntheses de tetrahydrodioxazine–1, 4,2 ones–3 et de carbomethoxy–2 tetrahydrodioxazines–1, 4,2, *Bulletin de la Societe Chimique de France, Partie II*, II–173–II–182, 1984.

G. Picciola, Sintesi de Acidi Chinazolinonici e Genzossazinonici e Studio Delle Loro Proprieta Antiinfiammatorie, *Il Farmaco, Edizione Scientifica*, 31, No. 9, 655–665, 1976.

* cited by examiner

*Primary Examiner*—Charles T. Jordan
*Assistant Examiner*—Glenda L. Sánchez

(57) ABSTRACT

Oxadiazines of formula I, wherein $R^1$ is F, Cl or fluoroalkoxy and $R^2$ is alkyl, are prepared by reacting hydrazine derivatives of formula II with a dialkoxymethane in the presence of a protic acid catalyst in an inert solvent under conditions which allow for the prompt removal of the alcohol by-product by distillation.

I

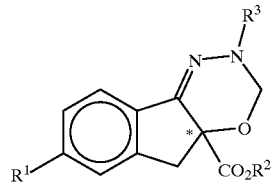

II

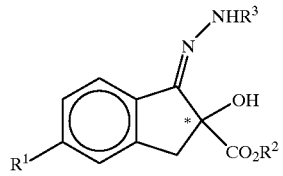

The reaction can be combined with the preparation of the hydrazines derivatives II from the corresponding ketones and hydrazines $NH^2$-$NHR^3$ in the presence of the same protic acid catalyst and an inert solvent. Oxadiazines I are useful as intermediates in the preparation of arthropodicidal agents.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESSES FOR PREPARING INDENO[1,2-E][1,3,4]OXADIAZINE-DICARBOXYLATES

CROSS REFERENCE TO RELATED APPLICATIONS

This application was filed under 35 U.S.C. 371 from PCT/US97/13548, filed Jul. 31, 1997, which claims priority from U.S. Provisional application Ser. No. 60/022,426, filed Aug. 5, 1996.

FIELD OF INVENTION

This invention relates to processes for preparing intermediates, particularly of dicarboxylate oxadiazines of Formula I and hydrazine carboxylates of Formula II, which are useful in the preparation of arthropodicidal oxadiazines.

BACKGROUND OF THE INVENTION

WO95/29171 discloses the preparation of arthropocidal oxadiazines from dicarboxylate oxadiazines of Formula I and hydrazine carboxylates of Formula II.

In WO95/29171, compounds of Formula I are prepared by reacting compounds of Formula II with a di($C_1$-$C_3$ alkoxy) methane in the presence of a Lewis acid, optionally in an inert solvent. The Lewis acids named are $P_2O_5$, $BF_3$, $SO_3$ (0.9 to 4.0 molar equivalent required) and metal trifluoromethanesulfonates (0.1 to 0.5 molar equivalent required). All of the specifically named solvents for this transformation are halogenated (dichloromethane, 1,2-dichloroethane, chlorobenzene, a,a,a -trifluorotoluene). It is stated that when a metal trifluoromethanesulfonate is employed, it is preferable to continuously remove the byproduct alcohol by distillation. In contrast, the process of the present invention allows for the use of a protic acid such as para-toluene sulfonic acid in catalytic quantities, such as 0.1 molar equivalent in a non-halogenated solvent (e.g. toluene) to provide good product quality in high chemical yield.

The need exists for a more efficient process to prepare oxadiazines of Formula I from hydrazine carboxylates of Formula II.

SUMMARY OF THE INVENTION

The present invention pertains to processes for preparing oxadiazine dicarboxylates of Formula I which are racemic or enantiomerically enriched at chiral center*

I

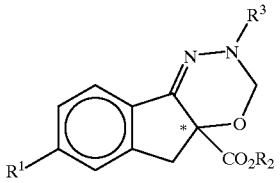

wherein $R^1$ is F, Cl, or $C_1$-$C_3$ fluoroalkoxy, $R^2$ is $C_1$-$C_3$ alkyl, and $R^3$ is a protecting group such as $CO_2CH_2(C_6H_5)$ comprising: reacting a compound of Formula II, which is racemic or enantiomerically enriched at*,

II

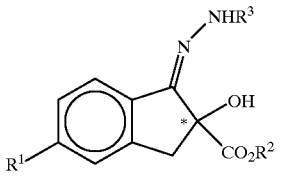

with a di($C_1$-$C_3$ alkoxy)methane in the presence of a protic acid catalyst in an inert solvent under conditions which allow for the prompt removal of the by-product alcohol by distillation.

This invention further pertains to processes for preparing compounds of Formula I as defined above comprising:

(a) reacting a compound of Formula III, which is racemic or enantiomerically enriched at*,

III

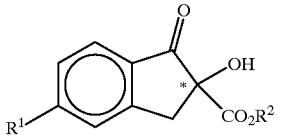

with the compound of Formula IV in the presence of a protic acid catalyst in an inert solvent $H_2NNHR^3$ IV to form a compound of Formula II

II

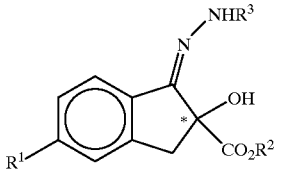

II and (b) reacting the compound of Formula II with a di($C_1$-$C_3$ alkoxy)methane in the presence of the same protic acid catalyst and inert solvent as used in step (a) under conditions which allow for the prompt removal of the by-product alcohol by distillation.

In the above recitations, the term "$C_1$-$C_3$ fluoroalkoxy" refers to methoxy, ethoxy, n-propoxy and iso-propoxy which may be partially or fully substituted with fluorine atoms. Examples of "fluoroalkoxy" include $CF_3O$ and $CF_3CH_2O$:

DETAILED DESCRIPTION OF THE INVENTION

The compounds of Formula I can be prepared by the process of this invention which comprises the process variations as described below.

Preferred compounds of Formula I are those where $R^1$ is F, Cl, $CF_3O$ or $CF_3CH_2O$, (more preferably Cl) and $R^2$ is $CH_3$.

Any protic acid can be used in the process of this invention as a catalyst. Suitable protic acid catalysts include mineral acids such as sulfuric acid and sulfonic acids such as aromatic, aliphatic and polymeric sulfonic acids. Preferred for reasons of greater commercial utility and/or ease of practice in the process for preparing compounds of Formula I are protic acids which do not co-distill to any significant extent with the by-product alcohol and which do not react with the dialkoxymethane to form products which could co-distill with the by-product alcohol. The preferred acids are those which catalyze both the reaction of compounds of Formula III with compounds of Formula IV, to give compounds of Formula II, and the conversion of compounds of Formula II to compounds of Formula I. Examples of the preferred acids are para-toluenesulfonic acid, mixtures of the isomeric toluenesulfonic acids, benzenesulfonic acid, naphthalene sulfonic acids, xylenesulfonic acids, methanesulfonic acid, sulfuric acid, and camphor sulfonic acids. Most preferred are para-toluenesufonic acid and mixtures of isomeric toluenesulfonic acids.

While stoichiometric or greater amounts of the protic acid can be employed, it is preferred for reasons of greater commercial utility and/or ease of practice in the process for preparing compounds of Formula I, from either compounds of Formula II or compounds of Formula III that a catalytic amount of the protic acid be employed. It is more preferred that a total of between 0.01 and 0.20 molar equivalent of protic acid, relative to the compound of Formula II or Formula III, be employed. Most preferred is the process in which between 0.05 to 0.10 molar equivalent of protic acid is employed. In general, the use of 0.05 to 0.10 molar equivalent of protic acid allows for useful reaction rates while minimizing acid use and waste generation.

The solvent used in the process of this invention can be any inert solvent which when combined with the reactants used in the process of the present invention forms a reaction mixture from which the alcohol produced as a by-product in the process of this invention, such as ethanol, can be promptly separated by distillation. Depending on the specific reaction conditions, the alcohol can be removed as: (a) the alcohol; (b) an azeotrope or mixture of the alcohol and di($C_1$-$C_3$ alkoxy)methane; (c) an azeotrope or mixture of the alcohol and solvent; or, (d) an azeotrope or mixture of the alcohol, di($C_1$-$C_3$ alkoxy) methane and solvent. Preferred for ease of operation, cost, toxicity and environmental reasons are non-halogenated solvents such as, aliphatic and aromatic hydrocarbons and alkyl nitriles. More preferred are aliphatic and aromatic hydrocarbons and alkyl nitriles with boiling points between 80 and 150° C. Most preferred are toluene, xylenes, heptane and acetonitrile.

The alcohol or alcohol-containing component can be distilled from the reaction mixtures using equipment and techniques known to those skilled the art. Equipment and procedures which allow for efficient removal of alcohol while minimizing co-distillation of di($C_1$-$C_3$ alkoxy) methane and/or solvent are preferred. This can be achieved using conventional fractional distillation equipment.

The reaction of compounds of Formula II with a di($C_1$-$C_3$ alkoxy)methane is most conveniently run at the boiling point of the reaction mixture at ambient pressure. Reaction temperatures need to be at least equal to the boiling point of the by-product alcohol (e.g., ethanol) or of the alcohol containing azeotrope or mixture being removed. Preferred for reasons of greater commercial utility and/or ease of practice in the process for preparing compounds of Formula I from compounds of Formula II is a reaction temperature from between about 40 and 150° C. that allows for distillation of by-product alcohol. More preferred is a reaction temperature between 60 and 130° C. Most preferred is a reaction temperature between about 80 and 120° C. The reaction may also be carried out at elevated or reduced pressure. The use of reduced pressure can be particularly advantageous when using higher boiling solvents.

The reaction of compounds of Formula III with the compound of Formula IV is conducted at a reaction temperature from about 40 to 120° C. More preferred is a reaction temperature from about 50 to 90° C. Although the reaction can be carried out a ambient pressure, the reaction may also be carried out at elevated or reduced pressure. The use of reduced pressure can be particularly advantageous when using solvents that have boiling points higher than the desired reaction temperature. When preparing compounds of Formula II from compounds of Formula III and the compound of Formula IV, it is preferable that the by-product water be removed from the reaction mixture prior to combination of the reaction mixture with the di($C_1$-$C_3$ alkoxy) methane. More preferably, the by-product water can be removed by distillation as it is formed.

In principle, only one molar equivalent of di($C_1$-$C_3$ alkoxy) methane is needed. However, sufficient di($C_1$-$C_3$ alkoxy) methane should be employed so as to allow for losses of di($C_1$-$C_3$ alkoxy) methane via co-distillation. Any practical amount of the di($C_1$-$C_3$ alkoxy)methane can be employed in the process of this invention and it can be used as the solvent for the reaction to convert compounds of Formula II to compounds of Formula I. For reasons of economy it is preferable to use between about 1 and 20 equivalents of the di($C_1$-$C_3$ alkoxy)methane in conjuction with an inert solvent. More preferably between 1 and 10 equivalents of the di($C_1$-$C_3$ alkoxy)methane can be employed, most preferably between 2 and 7 equivalents. Preferred are the di($C_2$-$C_3$ alkoxy) methanes because they are higher boiling than the $C_2$-$C_3$ alcohols which they produce in the course of the reaction. This allows for removal of alcohol by distillation without removing large amounts of the di($C_2$-$C_3$ alkoxy)methane. Diethoxymethane is most preferred di($C_2$-$C_3$ alkoxy) methane because of availability and low cost.

In the reactions of compounds of Formula II with a di($C_1$-$C_3$ alkoxy)methane, the reagents should be combined at a rate such that the by-product alcohol produced is promptly and efficiently removed to avoid the formation of side-reaction products which adversely affect the purity and yield of the desired product. In one embodiment, a slurry of the hydrazine carboxylate of Formula II containing all or part of the solvent and optionally containing all or part of the protic acid and all or part of the di ($C_1$-$C_3$ alkoxy) methane is added over time to a mixture of the balance of solvent, protic acid and di($C_1$-$C_3$ alkoxy) methane which has been preheated to the appropriate reaction temperature. In an alternative embodiment, the di($C_1$-$C_3$ alkoxy)methane can be added to a mixture of the hydrazine carboyxlates of Formula II, solvent and protic acid which has been preheated to the appropriate reaction temperature. When the protic acid and the di($C_1$-$C_3$ alkoxy)methane are combined and heated prior to combination with the hydrazine carboxylate of Formula II, it is preferable to distill out any alcohol produced by the reaction of the acid with the di($C_1$-$C_3$ alkoxy) methane as it is formed.

The present invention further pertains to processes for preparing compounds of Formula I comprising: Step (a) preparing compounds of Formula II from compounds of Formula III and Step (b) reacting the compounds of Formula II with a di($C_1$-$C_3$ alkoxy) methane under conditions which allow for prompt removal of the by-product alcohol by distillation wherein both steps are carried out in the presence of the same protic acid catalyst and inert solvent.

A compound of Formula I can be further converted to arthropodicidal oxadiazines of Formula VII by (a) hydrogenating the compound of Formula I to form a compound of Formula V

V

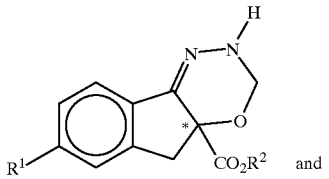

and (b) reacting the compound of Formula V with the compound of Formula VI

VI

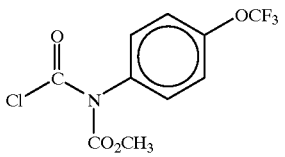

to form a compound of Formula VII having substantially the same absolute configuration as the compound of Formula I.

VII

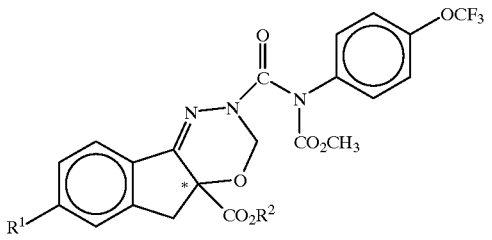

The preparation of the compound of Formula VI is described in WO 95/29171.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for the chromatographic solvent mixture which is by volume.

EXAMPLE 1

Preparation of 4a-methyl 2-(phenylmethyl)-7-chloroindeno[1.2-e][1,3,4]oxadiazine-2,4a(3H,5H)-dicarboxylate A 1 L, 4-neck round bottom flask (RBF) was equipped with an overhead stirrer with an oval paddle, thermometer, liquid feed line with an FMI (Fluid Metering Inc.) pump, 10 tray Oldershaw column equipped with a variable takeoff head, condenser and nitrogen inlet, and a heating mantel. The system was set up so that temperature could be monitored in the pot, at the 2, 4, 6, 8, 10 trays of the Oldershaw column and at the distillation head. Circulation of chilled water through the condenser was initiated. The flask was charged with 50 mL (0.4 mol) of Aldrich diethoxymethane and 100 mL of toluene and heated to reflux. The pot and head temperatures were 106° C. and 83° C., respectively. Column temperatures at the second, forth, sixth, eighth and tenth trays (from bottom to top) were 97° C., 93° C., 90° C., 88° C. and 83° C. In a separate flask, a mixture of 1.15 g of para-toluenesulfonic acid monohydrate and 125 mL of toluene was dried by azeotropic distillation of about 45 mL of the solvent using a Dean-Stark trap. The resulting mixture was allowed to cool to ambient temperature and 24.56 g (0.06 mol, 94.8% assay) of racemic phenylmethyl[5-chloro-2,3-dihydro-2-hydroxy-2-(methoxycarbonyl)-1 H-inden-1-ylidene]hydrazinecarboxylate disclosed in WO95/29171 added to give a slurry. This slurry was then pumped into the refluxing mixture of diethoxymethane and toluene over 2 hours and 24 minutes and rinsed in with toluene. Once the temperature at the eighth tray (counting from the bottom) of the column dropped below 80° C., takeoff ethanol/diethoxymethane/toluene distillate was initiated at such a rate as to maintain the temperature at the fourth tray at 79–83° C. After the addition of the slurry was complete, the distillate was slowly collected until the temperature at the eighth tray reached 88° C. The rate of take off was then increased and distillation continued until the head temperature reached 110° C. A total of about 117 mL (99.0 g) of distillate was collected. The reaction mixture was allowed to cool, and concentrated using a rotary evaporator; the residue was dissolved in ethyl acetate, filtered, and the filtrate concentrated using a rotary evaporator to leave 29.12 grams of oil. The oil was slurried with 75 mL of methanol and cooled in an ice bath. The crystals which formed were collected, washed with two 10 mL portions of cold methanol, and dried in a vacuum oven to give 21.0 grams (87% yield) of product which assayed (HPLC, 4.6×250 mm 5-micron, Zorbax® SB-C8 column and eluting at 1.5 mL/min. with 60% acetonitrile/40% water, 40° C., UV detector set at 254 nm) as 98.99% 4a-methyl 2-(phenylmethyl)-7-chloroindeno[1,2-e][1,3,4]oxadiazine-2,4a(3H,5 H)-dicarboxylate. m. p. 113–123° C.

EXAMPLE 2

Preparation of 4a-methyl 2-(phenylmethyl)-7-chlorindeno[1,2-e][1,3,4]oxadiazine-2,4a(3H,5H)-dicarboxylate A 1L, 4-neck RBF was equipped with an overhead stirrer with an oval paddle, thermometer, Dean-Stark trap, reflux condenser, and a heating mantel. The reactor was charged with 45.7 g (0.183 mol), 96.3% assay of racemic methyl 5-chloro-2,3-dihydro-2-hydroxy-1-oxo-1H-indene-2-carboxylate disclosed in WO 95/29171, 35.1 g (0.21 mol) of 99.4% phenylmethyl hydrazine carboxylate, 3.5 g (0.018 mol) of-para-toluene sulfonic acid monohydrate, and 235 mL of toluene. The mixture was heated to reflux for 7 h under a vacuum (~168 to 205 mm) sufficient to maintain the boiling point of the mixture between 65 and 72° C. During this time, 3.4 mL of water was collected in the Dean-Stark trap. Heating was discontinued and the flask returned to atmospheric pressure. On cooling to ambient temperature, the Dean-Stark trap and reflux condenser were removed and replaced with a 5 tray Oldershaw column equipped with a variable takeoff head, condenser and nitrogen inlet. The flask was further equipped with a liquid feed line with an FMI (Fluid Metering Inc.) pump. The system was set up so that temperature could be monitored in the pot, at each tray of the Oldershaw column and at the distillation head. Circulation of chilled water through the condenser was initiated and the reaction mixture heated to reflux. The pot and head temperatures were 113° C. and 110° C., respectively. Column temperatures (from bottom to top) were 111° C., 110° C., 110° C., 110° C., and 110° C. Diethoxymethane (68 mL, 0.54 mol) was then pumped into the reaction mixture at a steady rate over 1 h and 6 min. Once the temperature at the fourth tray (counting from the bottom) of the column dropped below 80° C., takeoff off ethanol/diethoxymethane/toluene distillate was initiated at such a rate as to maintain the temperature at the fourth tray at 77–84° C. After the addition was complete, distillate was slowly collected over 50 min until the temperature at the fourth tray reached 91° C. The rate of take off was then increased and distillation continued until the head temperature reached 108° C. A total of about 104 mL (84.9 g) of distillate was collected. The reaction mixture was allowed to cool, concentrated using a rotary evaporator, the residue dissolved in 210 mL of methanol and cooled in an ice bath. The crystals which formed were collected, washed with three 30 mL portions of cold methanol, and dried in a vacuum oven to give 61.17 g (82% yield) of tan product which assayed (HPLC, 4.6×250 mm 5-micron, Zorbax® SB-C8 column and eluting at 1.5 mL/min. with 60% acetonitrile/40% water, 40° C., UV detector set at 254 nm) as 96.98% 4a-methyl 2-(phenylmethyl)-7-chlorindeno[1,2-e][1,3,4] oxadiazine-2, 4a(3H,5H)-dicarboxylate. m.p. 120–122° C.

EXAMPLE 3

Preparation of 4a-methyl 2-(phenylmethyl)-7-chloroindeno[1,2-e]-[1,3,4]oxadiazine-2,4a(3H,5 H)-dicarboxylate Step A A 2 L, 4-neck round bottomed flask was equipped with: an overhead stirrer with an oval paddle; thermometer; a Dean-Stark trap with a reflux condenser and nitrogen inlet; and a heating mantel. The reactor was purged with nitrogen and charged with 583 g of toluene, 120.7 g (0.50 mol, 99.68% assay) of 62% ee 5-chloro-2,3-dihydro-2-hydroxy-oxo-1H-indene-2-carboxylate, 94.13 g (0.55 mol) of 97% benzyl carbazate and 9.65 g (0.05 mol) of 98.5% para-toluene sulfonic. The mixture was heated to reflux under a vacuum (about 184 mm) sufficient to give a boiling point of 70° C. After a total of 6 h at reflux, the reaction mixture was allowed to cool to room temperature. Just prior to use in Step B, 131.5 g of diethoxymethane was added to the slurry.

Step B

A 3 L, 4-neck round bottomed flask was equipped with: an overhead stirrer with an oval paddle; thermometer; 5 tray Oldershaw column equipped with a variable take off head, condenser and nitrogen inlet; and a heating mantel. The system was set up so that temperature could be monitored in the pot, at each tray of the Oldershaw column and at the distillation head. Circulation of chilled water through the condenser was initiated. The flask was charged with 26.3 g (0.25 mol) of Aldrich diethoxymethane and 580 g of toluene and heated to reflux with a boil up of about 35 mL/min. The pot and head temperatures were 1111° C. and 102° C., respectively. Column temperatures at the first, second, third, forth, and fifth trays (from bottom to top) were 109° C., 107° C., 106° C., 104° C. and 102° C. The Step A slurry was then metered into the boiling solution over 6 h and 20 min and rinsed in with a mixture of 50 g of toluene and 26.3 g of diethoxymethane. As the addition proceeded, temperatures in the column and at the distillation head decreased. Once the temperature at the forth tray (counting from the bottom) of the column dropped to 80° C., takeoff off ethanol/diethoxymethane/toluene distillate was initiated at such a rate as to maintain the temperature at the fourth tray at about 80 to 84° C. After the addition was complete, distillate was slowly collected until the temperature at the forth tray reached 101° C. Take off of distillate was discontinued for 10 min during which time the temperature at the forth tray stayed at 101° C. Take off was then resumed at an increased rate until the head temperature reached 109° C. A total of about 328 mL (249 g) of distillate was collected. The reaction mixture was allowed to cool and the solvent then removed by distillation at 35 mm Hg until the pot temperature reached 70° C. Ethanol (360 mL) was then added and the mixture heated to reflux for 1 hour and allowed to cool. When the temperature reached 40° C., 30 mL of water was added and the mixture cooled to about 0° C. The product was collected by filtration, displacement washed with four cold 50 mL portions of ethanol , and dried on the filter to give 176.9 g (85% yield) of product which assayed (HPLC, 4.6×250 mm 5-micron, Zorbax® SB-C8 column and eluting at 1.5 mL/min. with 60% acetonitrile/40% water, 40° C., UV detector set at 254 nm) as 96.91% 4a-methyl 2-(phenylmethyl)-7-chloroindeno[1,2-e][1,3,4]oxadiazine-2,4a(3H,5 H)-dicarboxylate with an ee of 70%. m. p. 103–120° C.

EXAMPLE 4

Preparation of 4a-methyl 2-(phenylmethyl)-7-chloroindeno[1,2-e][1,3,4]oxadiazine-2,4a(3H,5 H)-dicarboxylate Step A A 2 L, 4-neck round bottomed flask was equipped with: an overhead stirrer with an oval paddle; thermometer; a Dean-Stark trap with a reflux condenser and nitrogen inlet; and a heating mantel. The reactor was purged with nitrogen and charged with 583 g of toluene, 120.7 g (0.50 mol, 99.68% assay) of 62% ee 5-chloro-2,3-dihydro-2-hydroxy-oxo-1H-indene-2-carboxylate, 94.13 g (0.55 mol) of 97% benzyl carbazate and 4.85 g (0.05 mol) of 99% methane-sulfonic acid. The mixture was heated to reflux under a vacuum (about 184 mm) sufficient to give a boiling point of 70° C. After a total of 5.25 h at reflux, the reaction mixture was allowed to cool to room temperature. Just prior to use in Step B 131.5 g of diethoxymethane was added to the slurry.

Step B

A 3 L, 4-neck round bottomed flask was equipped with: an overhead stirrer with an oval paddle; thermometer; 5 tray Oldershaw column equipped with a variable take off head, condenser and nitrogen inlet; and a heating mantel. The system was set up so that temperature could be monitored in the pot, at each tray of the Oldershaw column and at the distillation head. Circulation of chilled water through the condenser was initiated. The flask was charged with 26.3 g (0.25 mol) of Aldrich diethoxymethane and 580 g of toluene and heated to reflux with a boil up of about 26 mL/min. The pot and head temperatures were 111° C. and 102° C., respectively. Column temperatures at the first second, third, forth, and fifth trays (from bottom to top) were 108° C., 107° C., 106° C., 103° C. and 102° C. The Step A slurry was then metered into the boiling solution over about 4 h and rinsed in with 50 g of toluene. As the addition proceeded, temperatures in the column and at the distillation head decreased. Once the temperature at the forth tray (counting from the bottom) of the column dropped to 80° C., takeoff off ethanol/diethoxymethane/toluene distillate was initiated at such a rate as to maintain the temperature at the fourth tray at about 78 to 82° C. After the addition was complete, distillate was slowly collected until the temperature at the forth tray reached 94° C. Take off was then resumed at an increased rate until the head temperature reached 108° C. A total of about 306 mL (234 g) of distillate was collected. The reaction mixture was allowed to cool and the solvent then removed by distillation at 35 mm Hg until the pot temperature reached 71° C. Ethanol (560 mL) was then added and the mixture heated to reflux until the all of the precipitated solids dissolved. The solution was then cooled to about 0° C. The product was collected by filtration, displacement washed with six cold 50 mL portions of ethanol , and dried to give 164.1 g of product 4a-methyl 2-(phenylmethyl)-7-chloroindeno[1,2-e][1,3,4]oxadiazine-2,4a(3H,5H)-dicarboxylate with a m. p. 104–123° C.

What is claimed is:

1. A process for the preparation of a dicarboxylate oxadiazine of Formula I

I

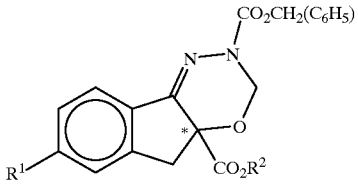

which is racemic or enantiomerically enriched at the chiral center*, wherein:

$R^1$ is F, Cl or $C_1$-$C_3$ fluroalkoxy and $R^2$ is $C_1$-$C_3$ alkyl comprising reacting a hydrazine carboxylate of Formula II

II

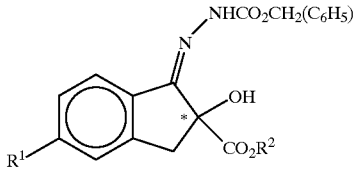

with at least one molar equivalent of a di($C_1$-$C_3$ alkoxy) methane in the presence of a protic acid catalyst in an inert solvent under conditions which allow for the prompt removal of the by-product alcohol by distillation.

2. A process of claim 1 wherein $R^1$ is Cl and $R^2$ is $CH_3$.

3. A process of claim 1 wherein the protic acid is selected from p-toluenesulfonic acid, mixtures of the isomeric toluene sulfonic acids, benzene sulfonic acid, napthalene sulfonic acids, xylene sulfonic acids, methanesulfonic acid, sulfuric acid and camphor sulfonic acids.

4. A process of claim 1 wherein a catalytic amount of the protic acid is used.

5. A process of claim 1 wherein the dialkoxy methane used is a di($C_2$-$C_3$ alkoxy) methane.

6. A process of claim 1 wherein the reaction temperature is from about 40–150° C. and at a pressure of about 1 atmosphere.

7. A process of claim 1 wherein the solvent is an inert non-halogenated solvent.

8. A process for preparing a compound of Formula I

I

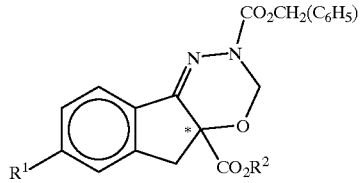

which is racemic or enantiomerically enriched at chiral center* wherein: $R^1$ is F, Cl, or $C_1$-$C_3$ fluoroalkoxy, and $R_2$ is $C_1$-$C_3$ alkyl, comprising:

(a) reacting a compound of Formula III, which is racemic or enantiomerically enriched at*,

III

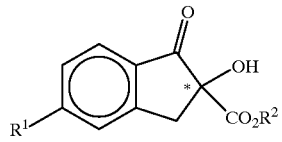

with the compound of Formula IV in the presence of a protic acid catalyst in an inert solvent $H_2N—NHCO_2CH_2(C_6H_5)$ IV to form a compound of Formula II

II

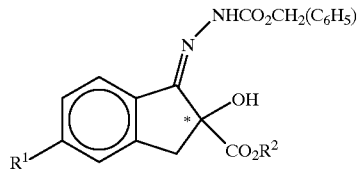

and (b) reacting the compound of Formula II with a di($C_1$-$C_3$ alkoxy) methane in the presence of the same protic acid catalyst and inert solvent as used in step (a) under conditions which allow for the prompt removal of the by-product alcohol by distillation.

9. A process of claim 1 further comprising the preparation of an arthropodicidal insecticide of Formula VII by (a) hydrogenating the compound of Formula I to form a compound of Formula V

V

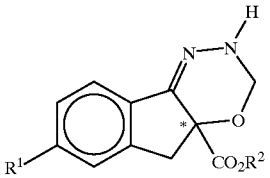

and (b) reacting the compound of Formula V with the compound of Formula VI

VI

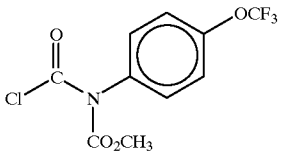

to form a compound of Formula VII having substantially the same absolute configuration as the compound of Formula I.

VII

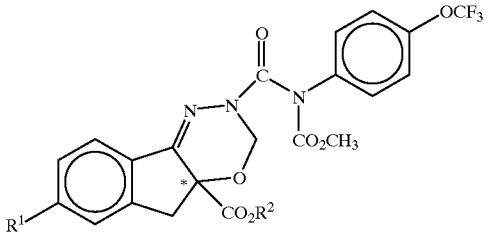

* * * * *